(12) United States Patent
Hopper

(10) Patent No.: US 12,017,051 B2
(45) Date of Patent: Jun. 25, 2024

(54) TRACK AND LOCKING MECHANISMS FOR INJECTION DEVICE

(71) Applicant: WEST PHARMACEUTICAL SERVICES, INC., Exton, PA (US)

(72) Inventor: Kevin Hopper, Athens, TX (US)

(73) Assignee: West Pharmaceutical Services, Inc., Exton, PA (US)

( * ) Notice: Subject to any disclaimer, the term of this patent is extended or adjusted under 35 U.S.C. 154(b) by 85 days.

(21) Appl. No.: 17/640,862

(22) PCT Filed: Sep. 9, 2020

(86) PCT No.: PCT/US2020/049796
§ 371 (c)(1),
(2) Date: Mar. 7, 2022

(87) PCT Pub. No.: WO2021/050448
PCT Pub. Date: Mar. 18, 2021

(65) Prior Publication Data
US 2022/0331525 A1    Oct. 20, 2022

Related U.S. Application Data

(60) Provisional application No. 62/897,550, filed on Sep. 9, 2019.

(51) Int. Cl.
*A61M 5/32*    (2006.01)
*A61M 5/315*   (2006.01)

(52) U.S. Cl.
CPC .......... *A61M 5/326* (2013.01); *A61M 5/3158* (2013.01); *A61M 5/3271* (2013.01);
(Continued)

(58) Field of Classification Search
CPC .............. A61M 5/3158; A61M 5/3271; A61M 2005/3247; A61M 2005/3267;
(Continued)

(56) References Cited

U.S. PATENT DOCUMENTS

2006/0030819 A1* 2/2006 Young ............... A61M 5/31596
604/187
2008/0228147 A1* 9/2008 David-Hegerich ... A61M 5/326
604/198
(Continued)

FOREIGN PATENT DOCUMENTS

EP         3047866 A1 * 7/2016 .............. A61M 5/20
WO      2019/068109 A1    4/2019

*Primary Examiner* — Kevin C Sirmons
*Assistant Examiner* — Alexandra Lalonde
(74) *Attorney, Agent, or Firm* — Blank Rome LLP

(57) ABSTRACT

An injection device includes a lower housing, a needle guard and an upper housing. With the upper housing in a pre-use position and the needle guard in a first position, an abutment body of an arm of the upper housing abuts a catch of the lower housing, preventing the upper housing from moving distally relative to the lower housing toward a dispensed position. Proximal movement of the needle guard from the first position to a second position thereof causes proximal movement of a camming ramp of a leg of the needle guard with respect to the catch and the abutment body such that the camming ramp engages the arm, thereby deflecting the abutment body radially outwardly by a distance sufficient to allow the abutment body to pass radially outside of the catch, and, in turn, permits the distal movement of the upper housing into the dispensed position of the upper housing.

18 Claims, 18 Drawing Sheets

(52) U.S. Cl.
CPC .............. *A61M 2005/3247* (2013.01); *A61M 2205/584* (2013.01)

(58) Field of Classification Search
CPC ...... A61M 2005/3264; A61M 5/31571; A61M 5/00; A61M 5/178; A61M 5/20; A61M 5/2033; A61M 5/24; A61M 5/28; A61M 5/31; A61M 5/31565; A61M 5/3221; A61M 5/3232; A61M 5/3234; A61M 5/3243; A61M 5/3257; A61M 5/326; A61M 5/3245; A61M 5/3269; A61M 5/3272; A61M 5/3273; A61M 5/32; A61M 5/3202; A61M 5/3205; A61M 5/321; A61M 2005/2006; A61M 2005/2013; A61M 2005/2026; A61M 2005/2073; A61M 2005/208; A61M 2005/3235; A61M 2005/3236; A61M 2005/3238; A61M 2005/3252; A61M 2005/3254; A61M 2005/3261; A61M 2005/3263; A61M 2005/3268; A61M 2005/2403; A61M 2005/2485; A61M 2005/2492; A61M 2205/584; A61M 2205/583

See application file for complete search history.

(56) References Cited

U.S. PATENT DOCUMENTS

| | | | | |
|---|---|---|---|---|
| 2009/0259196 | A1* | 10/2009 | Gratwohl | A61M 5/326 604/198 |
| 2011/0092915 | A1* | 4/2011 | Olson | A61M 5/3202 604/198 |
| 2017/0239427 | A1* | 8/2017 | Mehawej | A61M 5/3245 |
| 2017/0354791 | A1* | 12/2017 | Lewkonya | A61M 5/3129 |

* cited by examiner

TRACK AND LOCKING MECHANISMS FOR INJECTION DEVICE

CROSS-REFERENCE TO RELATED APPLICATIONS

This application is a National Stage of International Patent Application No. PCT/US2020/049796, filed on Sep. 9, 2020, which claims priority from U.S. Provisional Patent Application No. 62/897,550, filed on Sep. 9, 2019, the entire contents of which are incorporated by reference herein.

BACKGROUND OF THE DISCLOSURE

Embodiments described herein relate generally to track and locking mechanisms for an injection device, and more particularly, to track and locking mechanisms utilized with a manual injection device having a needle guard and multiple housing components that move relative to one another to facilitate the injection process.

It is desirable to provide a manual injection device that is easy-to-use but also reliably prevents accidental needle sticks both before and after an injection without active user intervention. In addition, it is desirable to provide a manual injection device that prevents reuse without active user intervention.

BRIEF SUMMARY OF THE DISCLOSURE

Briefly stated, one aspect of the present disclosure is directed to an injection device configured to administer a medication. The device includes a lower housing configured to coaxially support a medication-retaining syringe having a needle, such that the needle protrudes from a distal end of the lower housing when the syringe is installed in the lower housing. The lower housing includes at least one catch that extends at least partially radially outwardly and has a proximally facing surface. A needle guard is in coaxial sliding engagement with the lower housing, the needle guard being longitudinally movable relative to the lower housing in a proximal direction from a first position, wherein a distal end of the needle guard extends distally beyond the distal end of the lower housing and is configured to conceal a distal tip of the needle when the syringe is installed in the lower housing, to a second position, wherein the distal end of the needle guard is configured to expose the distal tip of the needle when installed. The needle guard includes a distal guard portion having a distally facing needle opening and at least one leg extending proximally and longitudinally from the distal guard portion. The at least one leg has a rim radially outwardly extending therefrom and a camming ramp radially outwardly extending from the leg and positioned distally from the rim. An upper housing includes at least one longitudinally extending arm defining an abutment body having a distally facing abutment surface, the upper housing being in coaxial sliding engagement with the lower housing and longitudinally movable relative to the lower housing in a distal direction from a pre-use position to a dispensed position. When the upper housing is in the pre-use position and the needle guard is in the first position, the distally facing abutment surface of the abutment body of the at least one longitudinally extending arm of the upper housing abuts the proximally facing surface of the at least one catch of the lower housing, preventing the upper housing from moving distally relative to the lower housing toward the dispensed position, and the radially outwardly extending camming ramp of the at least one leg of the needle guard is located distally of the at least one catch of the lower housing. Proximal movement of the needle guard from the first position to the second position thereof, and with respect to the upper housing, causes proximal movement of the camming ramp with respect to the at least one catch and the abutment body such that the camming ramp engages the at least one longitudinally extending arm, thereby deflecting the abutment body radially outwardly by a distance sufficient to allow the abutment body to pass radially outside of the at least one catch of the lower housing and, in turn, permitting distal movement of the upper housing relative to the lower housing into the dispensed position of the upper housing.

BRIEF DESCRIPTION OF THE DRAWINGS

The foregoing summary, as well as the following detailed description of aspects of the disclosure, will be better understood when read in conjunction with the appended drawings. It should be understood, however, that the disclosure is not limited to the precise arrangements and instrumentalities shown, and reference is made to the claims for that purpose. In the drawings:

DETAILED DESCRIPTION OF THE DISCLOSURE

Figure 1:
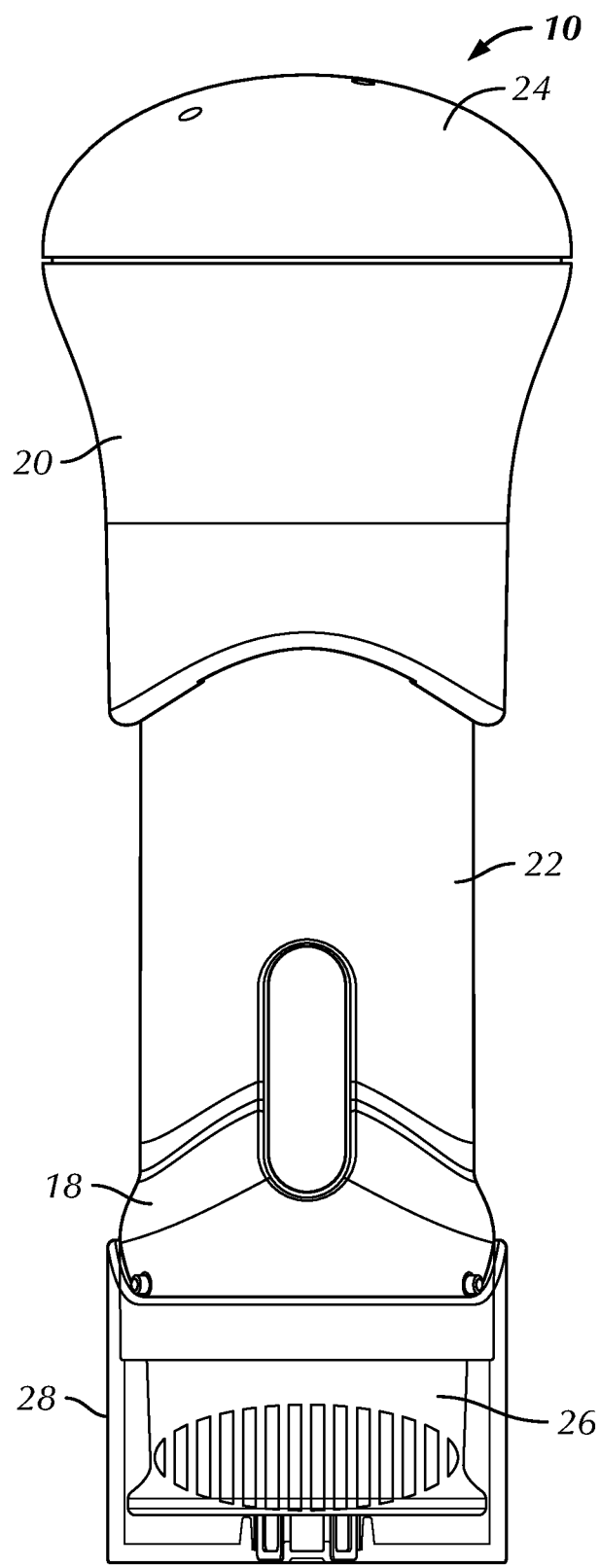
FIG. 1 is a front side elevational view of an injection device according to a first preferred embodiment.

Certain terminology is used in the following description for convenience only and is not limiting. The words "right", "left", "lower", and "upper" designate directions in the drawings to which reference is made. The words "inwardly" and "outwardly" refer to directions toward and away from, respectively, the geometric center of the device and designated parts thereof. The terminology includes the above-listed words, derivatives thereof, and words of similar import. Additionally, the words "a" and "an", as used in the claims and in the corresponding portions of the specification, mean "at least one."

It should also be understood that the terms "about," "approximately," "generally," "substantially" and like terms, used herein when referring to a dimension or characteristic of a component, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 2:
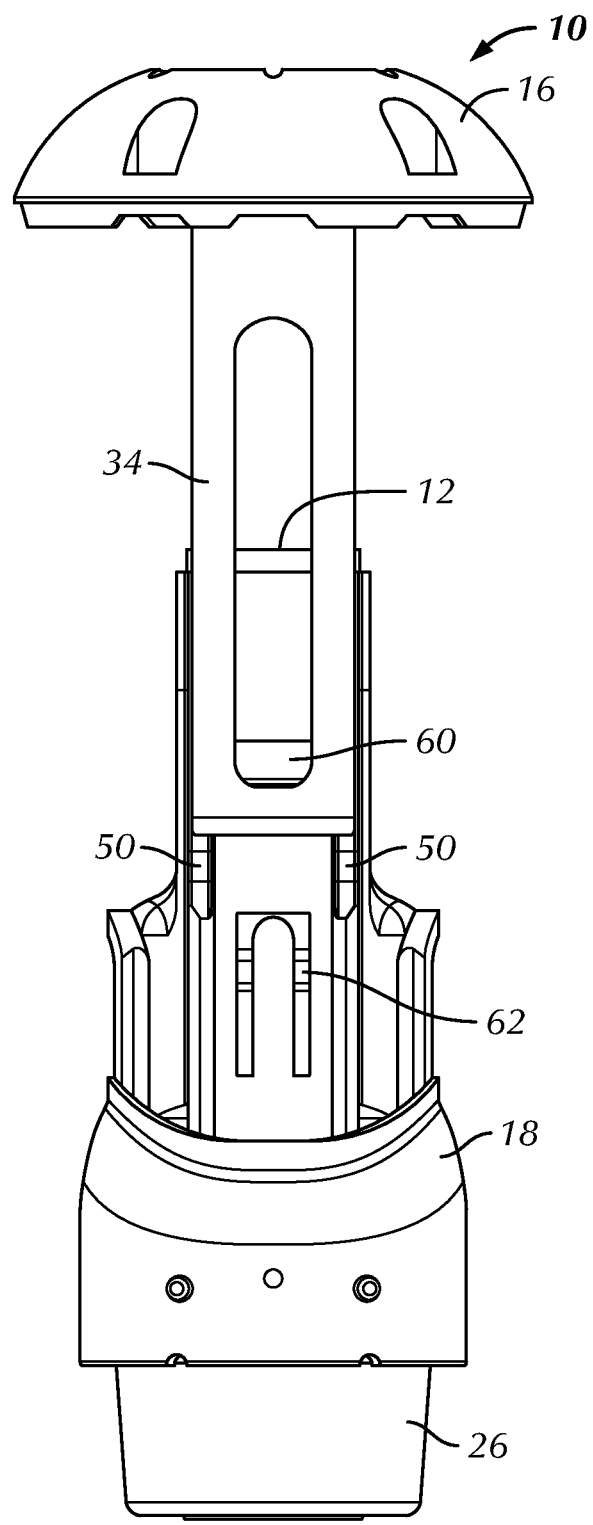
FIG. 2 is a left side elevational view of the injection device of FIG. 1 with a grip cap, upper shell, and lower shell removed.
Figure 7:
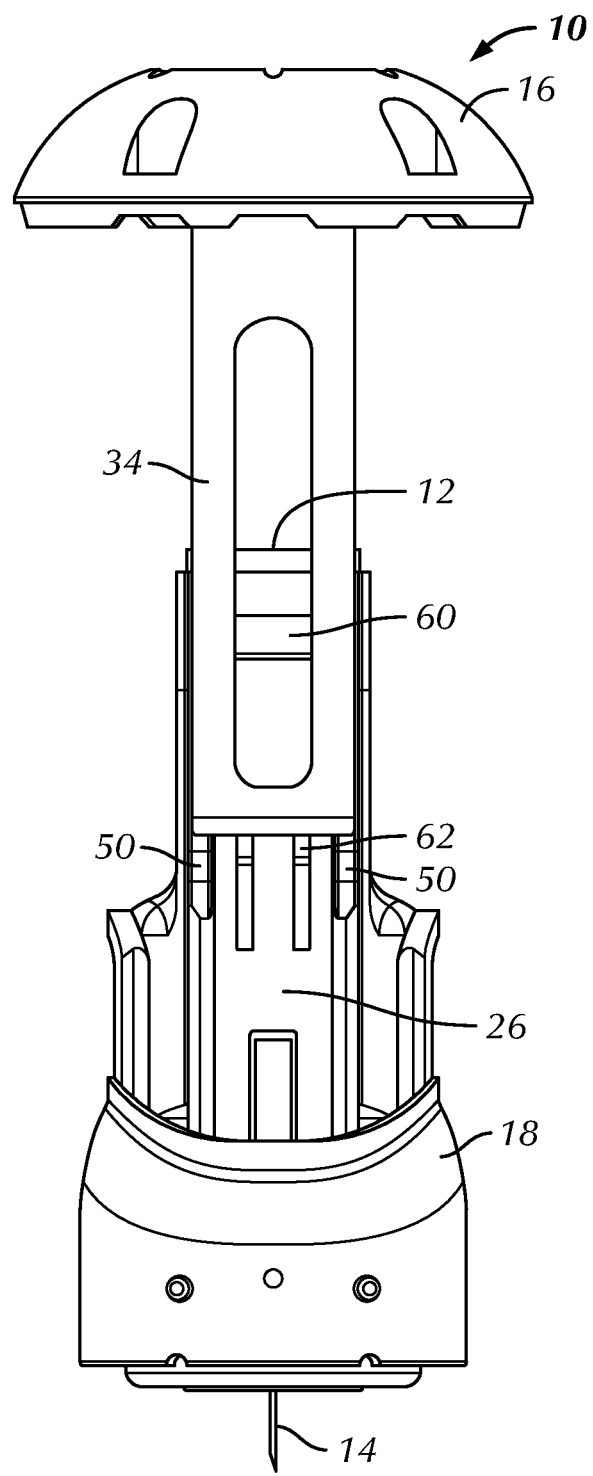
FIG. 7 is a left side elevational view of the injection device of FIG. 2 with the needle guard in a retracted position.

Referring to FIGS. 1-2, there is shown a first preferred embodiment of an injection device 10 for which the track and locking mechanisms described herein may be utilized. In the embodiment shown, the injection device 10 is a palm-actuated, manual injector containing a prefilled syringe 12 and an accompanying needle 14 (FIG. 7). The injection device 10 includes an upper housing 16 and a lower housing 18, which, as will be described in further detail below, are configured to be movable with respect to each other in a longitudinal direction during an injection. The prefilled syringe 12 may be retained coaxially within the lower housing 18 such that the needle 14 protrudes from a distal end of the lower housing 18. An upper shell 20 may be attached for movement with the upper housing 16 and similarly, a lower shell 22 may be attached for movement with the lower housing 18. The upper and lower shells 20, 22 may surround and prevent user access to particular components of the corresponding upper and lower housings 16, 18.

The upper housing 16 may also be provided with a grip cap 24 to facilitate handling and actuation of the injection device 10 by the user. The grip cap 24 may be affixed to the upper housing 16 for movement therewith. The grip cap 24 may include a plunger (not shown) which passes longitudinally through the upper housing 16 and into an open end of the prefilled syringe 12 such that movement of the upper housing 16 toward the distal end of the lower housing 18 causes medicament (not shown) to be expelled from the prefilled syringe 12 via the needle 14. Alternatively, the grip cap 24 and/or the plunger may be integrally formed with the upper housing 16. In another embodiment, the prefilled syringe 12 may include its own plunger, which is acted upon by a corresponding element (not shown) of the grip cap 24 and/or the upper housing 16.

The injection device 10 is further provided with a needle guard 26 at least partially coaxially oriented to, and longitudinally movable with respect to, the lower housing 18. The needle guard 26 is preferably biased, such as by a coil spring 27 (FIG. 11) or the like, to extend a distal end of the needle guard 26 distally beyond the distal end of the lower housing 18 in one or more extended positions, to prevent access to a tip of the needle 14. However, to allow for an injection, the needle guard 26 may be moved proximally toward the distal end of the lower housing 18, such as when the needle guard 26 is pressed against the skin of a patient, thereby exposing the needle 14 in a retracted position of the needle guard 26. As will be described in further detail below, the initiation of an injection, even if not taken to completion, may allow the needle guard 26 to be locked in place with respect to the lower housing 18 upon return to an extended position, thereby preventing re-use of the injection device 10 and preventing access to the needle 14.

A needle shield puller 28 (see FIG. 1) may be removably attached to a distal end of the lower housing 18. The needle shield puller 28 may be coupled to a rigid needle shield (not shown) or the like that initially covers the needle 14 of the prefilled syringe 12. Removal of the needle shield puller 28 from the lower housing 18 causes the rigid needle shield to detach from the prefilled syringe 12 and expose the needle 14 within the injection device 10 for use.

Figure 3:
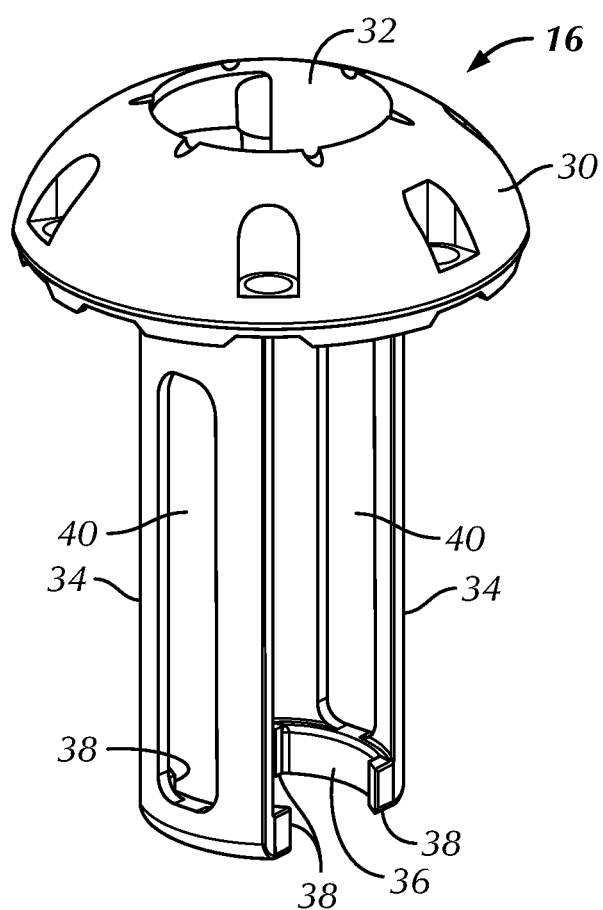
FIG. 3 is a front left perspective view of an upper housing of the injection device of FIG. 1.

Referring to FIG. 3, an exemplary embodiment of the upper housing 16 is shown and may include a head portion 30 at a proximal end thereof to which the grip cap 24 (FIG. 1) may be attached when the injection device 10 is assembled. In the embodiment shown, the head portion 30 includes a plunger opening 32 that is sized and shaped to allow the plunger from the grip cap 24 to be inserted therethrough. In other embodiments, the plunger or an element configured to manipulate a plunger of the prefilled syringe 12, may be attached directly to the head portion 30 of the upper housing 16. The plunger opening 32 may further be sized and shaped to allow insertion of the prefilled syringe 12 into the lower housing 18 when the injection device 10 is partially assembled.

The upper housing 16 may further include at least one arm 34 that is attached to, and longitudinally extends in a distal direction from, the head portion 30. In the embodiment shown in FIG. 3, two arms 34 are provided circumferentially spaced apart from one another on opposing sides of a central longitudinal axis of the upper housing 16. While each arm 34 may take a planar form, the arms 34 in FIG. 3 exhibit a slight curvature relative to the central longitudinal axis. The geometry is preferably configured to mate with the lower housing 18 and needle guard 26 to allow relative longitudinal motion among the three components. Optionally, a distal end of each arm 34 may include an abutment surface in the form of a radially-inwardly extending ledge 36 that may span a circumferential width of the arm 34 and terminates on both sides in a locking tab 38 that extends at least partially further radially inwardly from the respective ledge 36. In some embodiments, the ledge 36 itself may serve the function of the locking tabs 38 such that the locking tabs 38 are not necessary. In other embodiments, one or more locking tabs 38 may be located other than at ends of the ledge 36, such as in a middle portion of the ledge 36, or the like. Each arm 34 may also include a track window 40 that extends longitudinally along a portion of the arm 34. Depending on the sizes and thicknesses of various components of the injection device 10, the track window 40 can alternatively be formed as a groove (not shown) on an interior surface of the corresponding arm 34 or can be omitted altogether.

Figure 4:
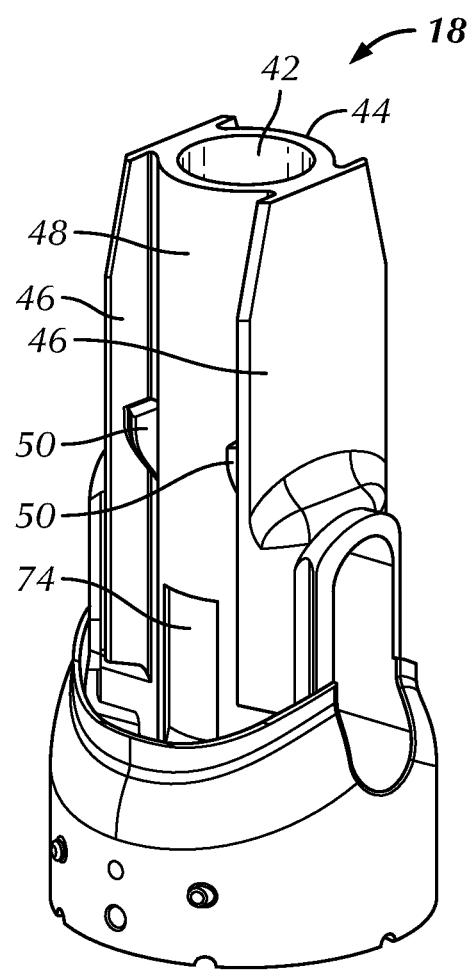
FIG. 4 is a front left perspective view of a lower housing of the injection device of FIG. 1.

Referring to FIG. 4, an exemplary embodiment of the lower housing 18 is shown. The lower housing 18 includes a central, longitudinally extending bore 42 which receives and supports the prefilled syringe 12 (not shown in FIG. 4). In the present example, a flange of the prefilled syringe 12 may contact and rest upon a proximally facing annular surface 44 of the lower housing 18. Additional components may be used to prevent distal motion of the prefilled syringe 12 relative to the lower housing 18, such as, for example, securing arms as described in PCT Application Publication No. WO2019/068109, snaps, frictional fittings, or the like. While not shown in FIG. 4, the needle 14 preferably protrudes from the distal end of the lower housing 18 when the prefilled syringe 12 is installed.

The lower housing 18 further includes a pair of circumferentially spaced apart and longitudinally extending track walls 46. The track walls 46 bracket at least one longitudinally extending track 48, which is sized and shaped to receive a corresponding arm 34 of the upper housing 16 for longitudinal movement therein. The track walls 46 may prevent relative rotation of the upper and lower housings 16, 18 by abutting or containing longitudinal edges of the arms 34. At least one track 48 may include a catch 50 located between proximal and distal ends of the track 48. Each catch 50 extends at least partially radially outwardly. As will be described in further detail below, a proximally facing surface of each catch 50 is configured to abut a distally facing surface of a corresponding locking tab 38 of the upper housing 16 in an initial position of the injection device 10 to prevent relative longitudinal motion of the upper and lower housings 16, 18 until an injection is ready to be made.

Figure 5:
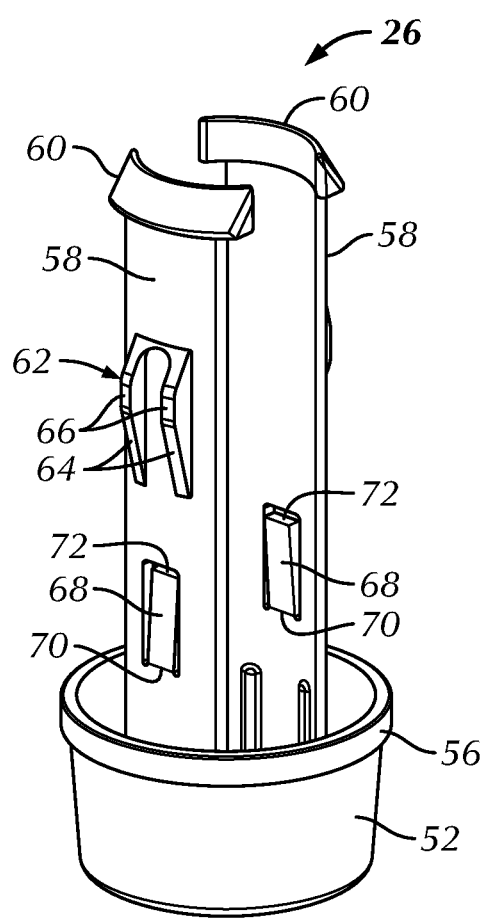
FIG. 5 is a front left perspective view of a needle guard of the injection device of FIG. 1.

Referring to FIG. 5, an exemplary embodiment of the needle guard 26 is shown. The needle guard 26 includes a guard portion 52 at a distal end thereof. A distally facing surface of the guard portion 52 includes a needle opening 54 (see FIG. 11), which allows passage of the needle 14 therethrough when an injection is to be made. The needle opening 54 may be generally sized to prevent insertion of a finger therein when the needle guard 26 is in an extended, first position with respect to the lower housing 18. Moreover, the needle guard 26 may be biased toward this extended position by a coil spring 27 or other type of biasing device coupled between the needle guard 26 and the lower housing 18. Specifically, the needle guard 26 is configured for longitudinal movement with respect to the lower housing 18, so that at least a section of the guard portion 52 may be at least partially retracted into the lower housing 18 to expose the needle 14 through the needle opening 54.

The guard portion 52 further may include a visual indicator 56 to signify to the user that an injection has been completed and the injection device 10 is locked to prevent reuse. In the embodiment shown, the visual indicator 56 may take the form of an annular ring having a larger radial thickness than a remainder of the guard portion 52, and may also have a different color. Moreover, as will be described more fully below, it is preferred that the visual indicator 56 remain obscured from view by the lower housing 18 until after injection has been completed. In other embodiments, the guard portion 52 may be sized to obscure the distal end of the lower housing 18 during relative longitudinal movement of the two components.

The needle guard 26 further includes at least one leg 58 attached to and extending longitudinally in a proximal direction from the guard portion 52. In the embodiment shown in FIG. 5, two legs 58 are provided circumferentially spaced apart from one another on opposing sides of a central longitudinal axis of the needle guard 26. While each leg 58 may take a planar form, the legs 58 in FIG. 5 exhibit a slight curvature relative to the central longitudinal axis. The geometry is preferably configured to mate with the upper housing 16 and lower housing 18 to allow relative longitudinal motion among the three components. A proximal end of each leg 58 may include a radially-outwardly extending rim 60, e.g. a barbed rim 60, that may span a circumferential width of the leg 58 or may extend either less than the circumferential width of the leg 58 or slightly beyond the circumferential width.

Each leg 58 may be provided with a cam/camming ramp 62 positioned distally from the rim 60 and which extends radially outwardly from the leg 58. In the embodiment of FIG. 5, the cam ramp 62 takes the form of a pair of circumferentially spaced apart, longitudinally extending ridges 64, each having a generally central plateau 66 away from which the ridge 64 gradually slopes in both proximal and distal directions. The cam ramp 62 may be sized and shaped so as to fit and be movable within the track window 40 of the upper housing 16, as will be described in further detail below.

Each leg 58 may also be equipped with at least one locking finger 68. In the embodiment shown in FIG. 5, the locking finger 68 is attached to the leg 58 via a hinge 70, and extends longitudinally in the proximal direction toward a free end 72. The hinge 70 may be a living hinge, or the locking finger 68 may be a separate piece of material from the leg 58 that is pivotably attached thereto. In alternative embodiments, the orientation of the locking finger 68 can also be changed without departing from the scope of the invention. The locking finger 68 is preferably biased radially inwardly, so that the free end 72 thereof is located closer to a central longitudinal axis of the needle guard 26 than an inner surface of the corresponding leg 58. However, the locking finger 68 is preferably configured to allow radial movement of the free end 72 thereof. As will be described in more detail below, the flexibility of the locking finger 68 and the bias direction of the free end 72 enable the needle guard 26 to lock in place following completion of injection.

Figure 6:
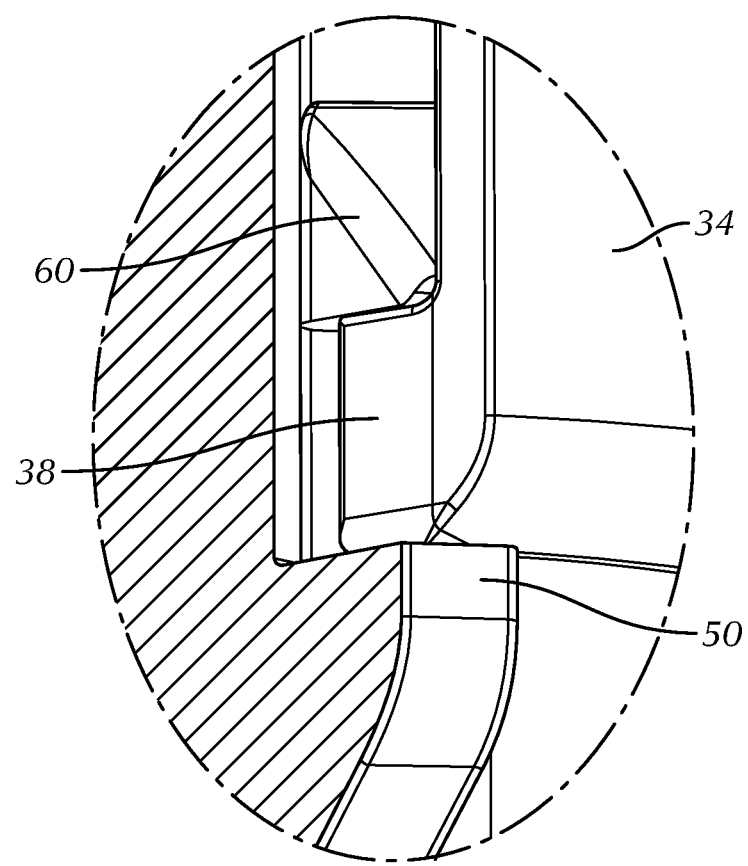
FIG. 6 is a greatly enlarged, partial cross-sectional left side perspective view of the upper housing, lower housing, and needle guard of the injection device of FIG. 1 in an initial position.

FIGS. 1 and 2 show the injection device 10 in an initial, pre-use position, i.e., prior to start of an injection. In operation, the upper housing 16 is preferably prevented from moving toward the distal end of the lower housing 18 until the needle guard 26 is at least partially retracted and/or the needle 14 is exposed. As can be seen in FIGS. 2 and 6, in the initial position, a distally facing surface of each locking tab 38 of the upper housing 16 abuts a proximally facing surface of a corresponding catch 50 of the lower housing 18. Thus, distally directed pressure on the upper housing 16 will be unable to advance the upper housing 16 toward the distal end of the lower housing 18, and will consequently prevent advancement of the plunger through the prefilled syringe 12 prior to the time of injection. Although not shown, interaction of the upper and lower shells 20, 22 may be used to prevent the upper housing 16 from being pulled proximally away from the lower housing 18 in this initial position.

Additionally, a distally facing surface of the rim 60 of the leg 58 of the needle guard 26 preferably abuts a proximally facing surface of the locking tab 38 and/or the ledge 36 of the arm 34 of the upper housing 18 when the injection device 10 is in the initial position. This prevents the needle guard 26 from moving any further distally with respect to the lower housing 18 prior to the start of injection, which as will be described in further detail below, prevents the needle guard 26 from locking out prematurely. As seen in FIG. 2, in the initial position, the cam ramp 62 of the needle guard 26 is located distally of the catches 50 on the lower housing 18.

A user initiates an injection with the injection device 10 by placing the distal end of the needle guard 26 at the injection site (not shown) and applying distally directed pressure to the injection device 10, preferably via the grip cap 24. This force initially urges the needle guard 26 proximally with respect to the lower housing 18 toward a retracted, second position, for example, as shown in FIG. 7. The distal end of the needle 14 is eventually exposed through the needle opening 54 of the needle guard 26 and is directed into the injection site. With the upper housing 16 initially locked in place by the catches 50, the needle guard 26 also moves proximally with respect to the upper housing 16 during the application of the injection device 10 to the injection site. Thus, the cam ramp 62 on the lower housing moves proximally with respect to the catches 50 on the lower housing 18 and the distal end of the arm 34 of the upper housing 16. As the cam ramp 62 passes the proximally facing surfaces of the catches 50, the cam ramp 62 preferably interacts with the ledge 36 on the arm 34 of the upper housing 16, urging the ledge 36 and the distal end of the arm 34 radially outwardly.

When the needle guard 26 reaches its retracted position, the plateau 66 of the cam ramp 62 is preferably in contact with the ledge 36 of the arm 34 of the upper housing 16. This interaction preferably displaces the ledge 36 radially outwardly by a distance sufficient to allow the locking tabs 38 to release from the catches 50 on the lower housing 18. In this way, further distally directed pressure on the grip cap 24 results in movement of the upper housing 16 toward the distal end of the lower housing 18, as the locking tabs 38, with the ledge 36 riding along the cam ramp 62, pass radially outside of the catches 50. The arm 34 therefore moves distally with respect to the lower housing 18 unimpeded. As the ledge 36 distally clears the cam ramp 62, the ledge 36 and distal end of the arm 34 return to their original position, and the cam ramp 62 enters the track window 40 of the arm 34 (e.g., FIG. 8) so as to avoid further radial interaction with the arm 34 during the injection. Consequently, the plunger on the grip cap 24 moves distally within the prefilled syringe 12, expelling the medication through the needle 14 and into the patient.

Figure 8:
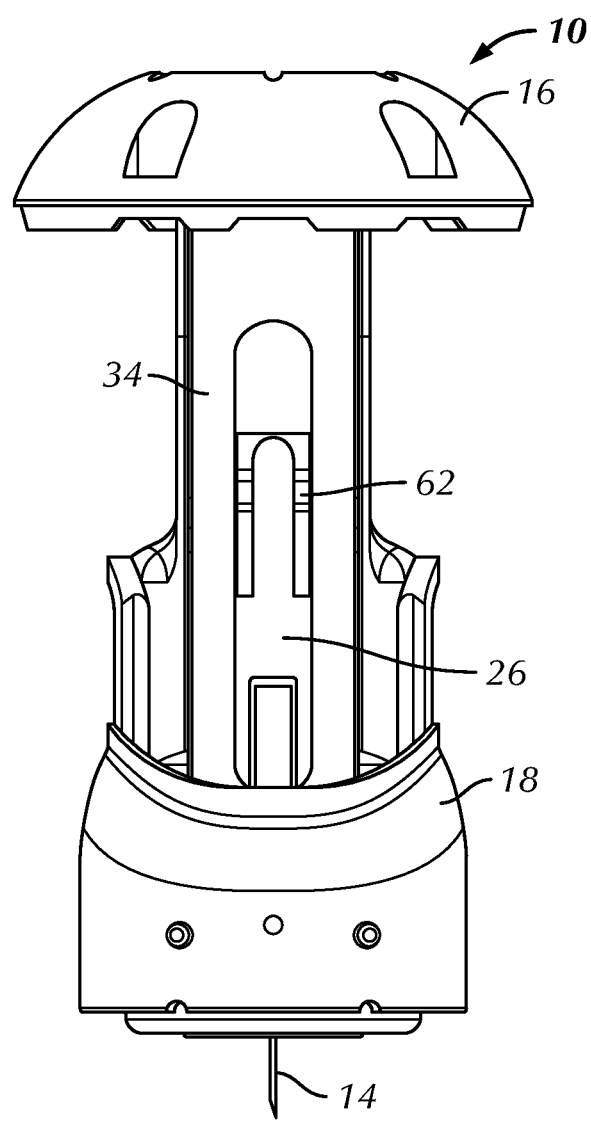
FIG. 8 is a left side elevational view of the injection device of FIG. 2 following injection and with the needle guard in the retracted position.

FIG. 8 shows an exemplary embodiment of the injection device 10 following completion of injection while the needle guard 26 is still in a retracted position on the injection site. The upper housing 16 reaches the fullest extent of its longitudinal travel with respect to the lower housing 18, preferably when the plunger abuts a distal interior end of the prefilled syringe 12, although other components (not shown) of the device 10 can alternatively be utilized to end the injection process. The upper housing 16 may be automatically locked to the lower housing 18 at this point, which will be described in further detail below. However, the needle guard 26 remains free to move distally with respect to the upper and lower housings 16, 18, as occurs when the injection device 10 is removed from the injection site and the needle guard 26 is acted upon by the biasing spring 27 or other similar device to return the needle guard 26 to an extended position.

Figure 9:
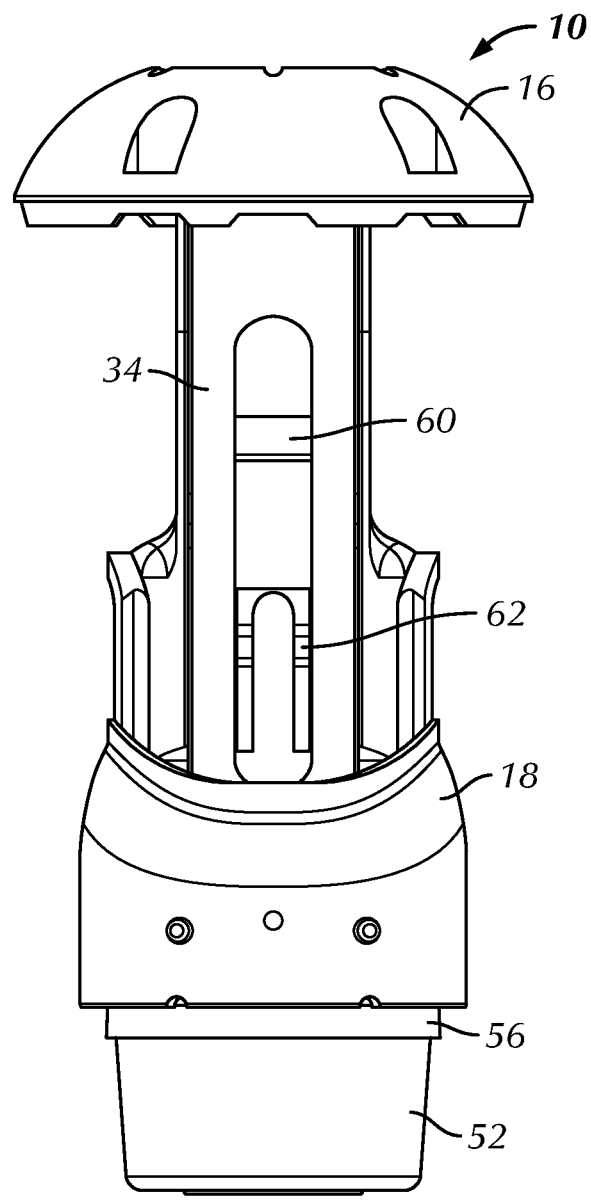
FIG. 9 is a left side elevational view of the injection device of FIG. 2 in a locked position.
Figure 10:
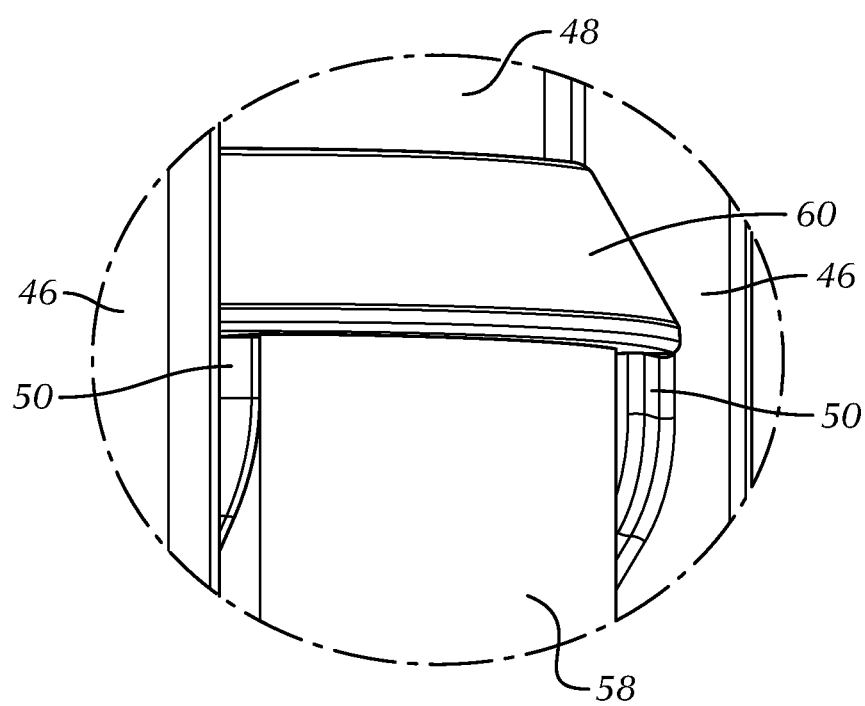
FIG. 10 is a greatly enlarged, partial left side perspective view of the lower housing and the needle guard in the locked position of FIG. 9.

FIG. 9 shows an exemplary embodiment of the injection device 10 in the locked position following removal thereof from the injection site. Distal movement of the needle guard 26 with respect to the lower housing 18 allows the guard portion 52 to again cover the needle 14. With the ledge 36 and locking tabs 38 of the upper housing 16 in a different location following injection, the rim 60 of the leg 58 of the needle guard 26 is preferably able to travel further distally than before, with the distally facing surface of the rim 60 being able to abut the proximally facing surfaces of the catches 50 on the lower housing 18, as shown in FIG. 10. This additional distance allows the visual indicator 56 on the guard portion 52 to be exposed from the lower housing 18, and provides additional protective distance between the distal end of the needle guard 26 and the distal end of the needle 14. The interaction between the rim 60 and the proximally facing surfaces of the catches 50 also preferably prevents the needle guard 26 from being removed distally from the lower housing 18.

Figure 11:
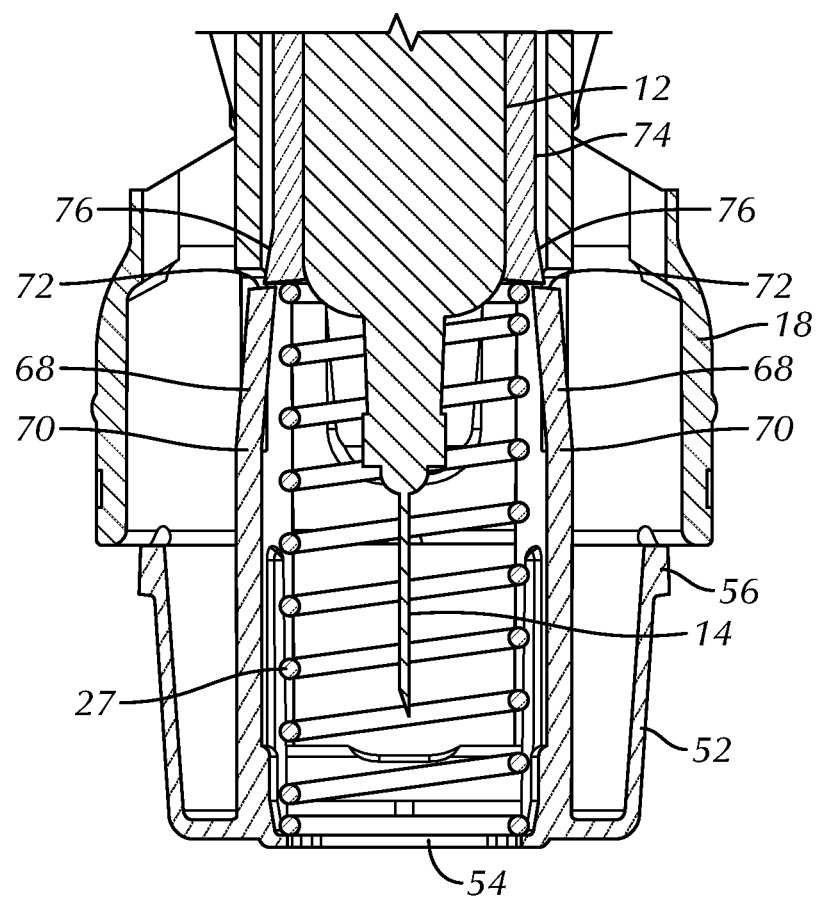
FIG. 11 is an enlarged, front side elevational cross-sectional view of the injection device of FIG. 2 in the locked position.

The additional distal travel distance of the needle guard 26 with respect to the lower housing 18 also enables locking of the needle guard 26 using the locking fingers 68 described above, to prevent subsequent access to the needle 14. Prior to and during injection, the free ends 72 of the locking fingers 68 preferably ride along corresponding radially outwardly facing surfaces of the tracks 48 of the lower housing 18. Each track 48 surface preferably deflects the respective free end 72 of the locking finger 68 radially outwardly. Referring back to FIG. 4, the lower housing 18 may also have a radially inwardly indented section 74 arranged in the track 48 within which the free end 72 of the locking finger 68 may move during the injection process. Referring to FIG. 11, the lower housing 18, and in particular the indented section 74, may have a radially outwardly inclined locking edge 76. As the needle guard 26 is withdrawn from the injection site and the needle guard 26 moves distally with respect to the lower housing 18, the additional distal travel distance allows the free ends 72 of the locking fingers 68 to move distally past the locking edges 76, at which point the radially inward bias of the free ends 72 allows the locking fingers 68 to return to a rest position, as shown in FIG. 11. At this point, abutment of proximally facing surfaces of the free ends 72 of the locking fingers 68 with distally facing surfaces of the locking edges 76 prevents the needle guard 26 from moving proximally with respect to the lower housing 18, keeping the needle 14 protected subsequent to injection.

Figure 12:
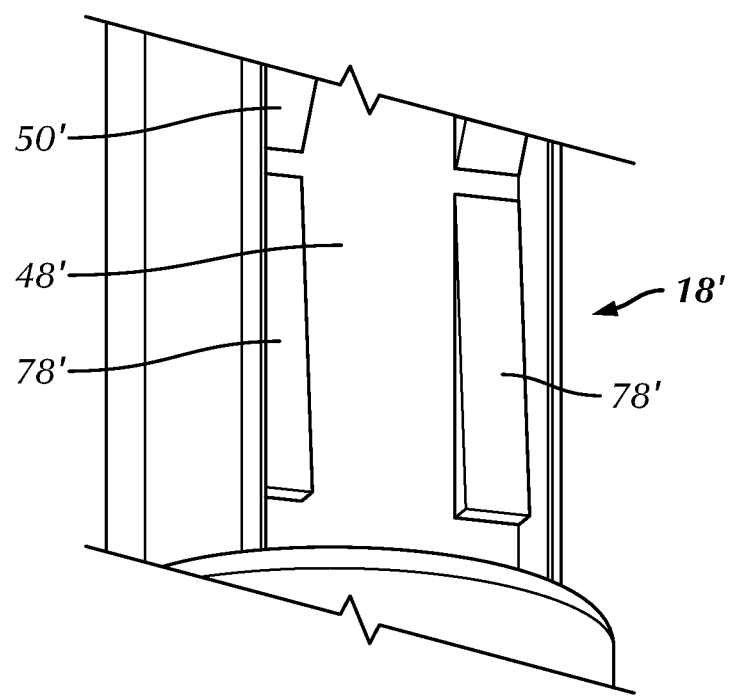
FIG. 12 is a greatly enlarged, partial left side perspective view of a lower housing in accordance with a second embodiment.

In some embodiments, it may be desirable following injection to prevent the upper housing 16 from being returned to its original position with respect to the lower housing 18, i.e., it may be desirable to have the upper housing 16 remain in the position shown in FIG. 9. FIG. 12 shows an embodiment of the lower housing 18' wherein a pair of locking ramps 78' are provided distally of the catches 50' and longitudinally extend along a distal portion of the track 48'. The locking ramps 78' are configured to gradually engage and move respective locking tabs 38 of the upper housing 16 generally radially outwardly during distal travel of the upper housing 16 with respect to the lower housing 18'. When the locking tabs 38 move distally past distal ends of the respective locking ramps 78', the locking tabs 38 become trapped, wherein abutment of proximally facing surfaces of the locking tabs 38 with distally facing surfaces of the locking ramps 78' prevent proximal movement of the upper housing 16 with respect to the lower housing 18'. However, other methods for locking the upper housing 16 in place with respect to the lower housing 18, 18' can be used as well.

Another exemplary embodiment is shown in FIGS. 13-18. The embodiment in FIGS. 13-18 is similar to the exemplary embodiment described above. Like numerals have been used for like elements, except the 100 series numerals have been used for the embodiment shown in FIGS. 13-18. Accordingly, a complete description of the embodiment has been omitted, with only the differences being described.

Figure 13:
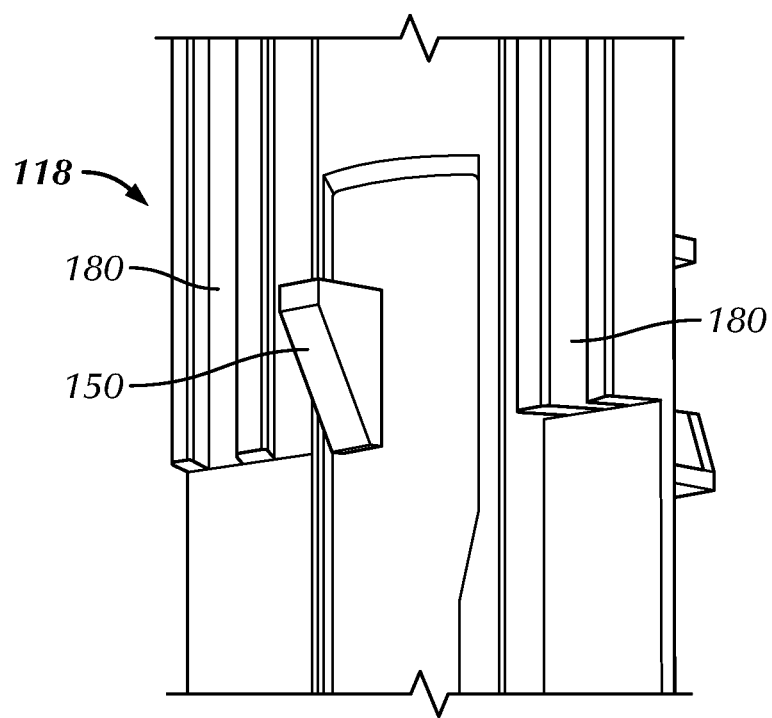
FIG. 13 is an enlarged, partial left side perspective view of a portion of a lower housing in accordance with a third embodiment.

A portion of the lower housing 118 is shown in FIG. 13, which includes a pair of opposed, longitudinally extending rails/tracks 180 formed thereon. The rails 180 are sized and shaped to receive longitudinal edges of arms 134 of the upper housing 116 (FIG. 14) to facilitate sliding relative movement of the upper and lower housings 116, 118. A catch 150, extending at least partially radially outwardly from the lower housing 118, is preferably positioned between the rails 180.

Figure 14:
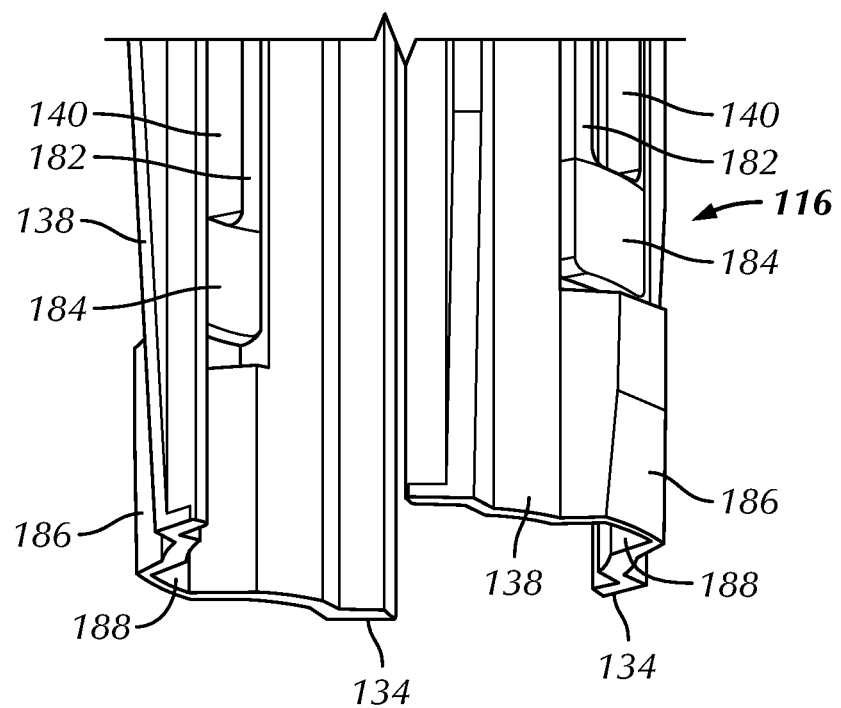
FIG. 14 is an enlarged, partial left side perspective view of an upper housing in accordance with the third embodiment.

Referring to FIG. 14, a portion of the upper housing 116 is shown, and specifically distal ends of the longitudinally extending arms 134. In the embodiment shown, each arm 134 includes a longitudinally extending flap 182 with a distally located abutment surface in the form of a free end 184. The free end 184 of the flap 182 is located proximate a bridge 186 formed at the distal end of the arm 134. The bridge 186 extends further radially outwardly than the free end 184 of the flap 182, leaving a pocket 188. The flap 182 further includes a longitudinally extending track window 140 formed therethrough.

Figure 15:
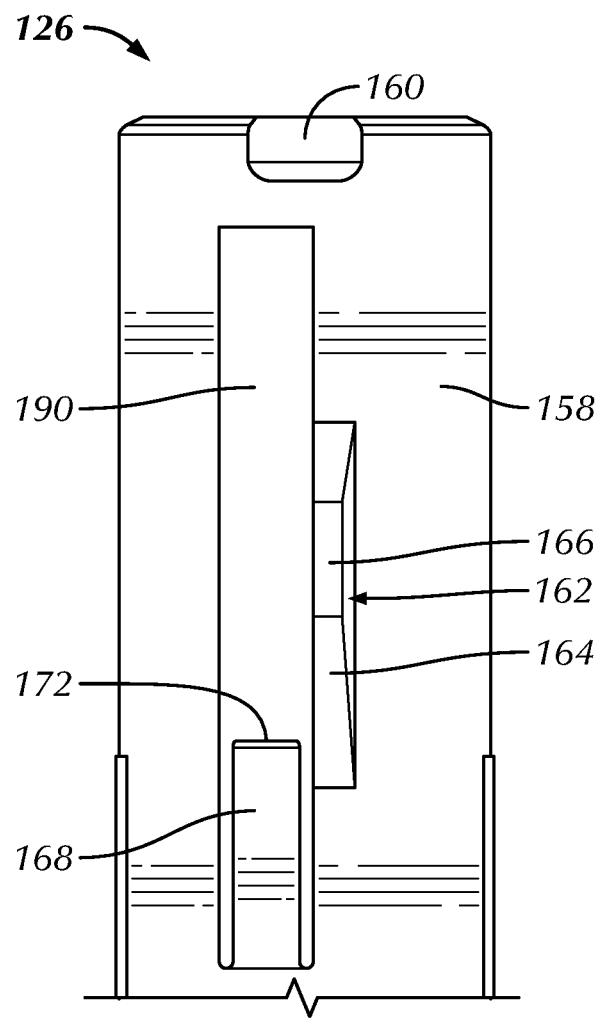
FIG. 15 is an enlarged, partial left side elevational view of a needle guard in accordance with the third embodiment.

FIG. 15 shows a portion of the needle guard 126, and specifically a proximal end of a leg 158. A proximal end of the leg 158 may include a radially-outwardly extending rim 160. Unlike the earlier embodiment, the rim 160 in FIG. 15 preferably does not extend to the full circumferential width of the leg 158. Rather, the rim 160 is preferably sized to fit within the track window 140 in the upper housing 116 for sliding movement therein. The leg 158 also preferably includes a cam/camming ramp 162 positioned distally from the rim 160 and which extends radially outwardly from the leg 158. In the embodiment of FIG. 15, the cam ramp 162 is in the form of a single, longitudinally extending ridge 164, having a generally central plateau 166 away from which the ridge 164 gradually slopes in both proximal and distal directions. The cam ramp 162 may be sized and shaped so as to fit and be movable within the track window 140 of the upper housing 116. The leg 158 may also include a longitudinally extending aperture 190 formed therein. When assembled, the catch 150 on the lower housing 18 may extend radially through the aperture 190 of the needle guard 126. The locking finger 168 is also visible in FIG. 15, and is shown extending longitudinally within the aperture 190 toward a proximal free end 172.

Figure 16:
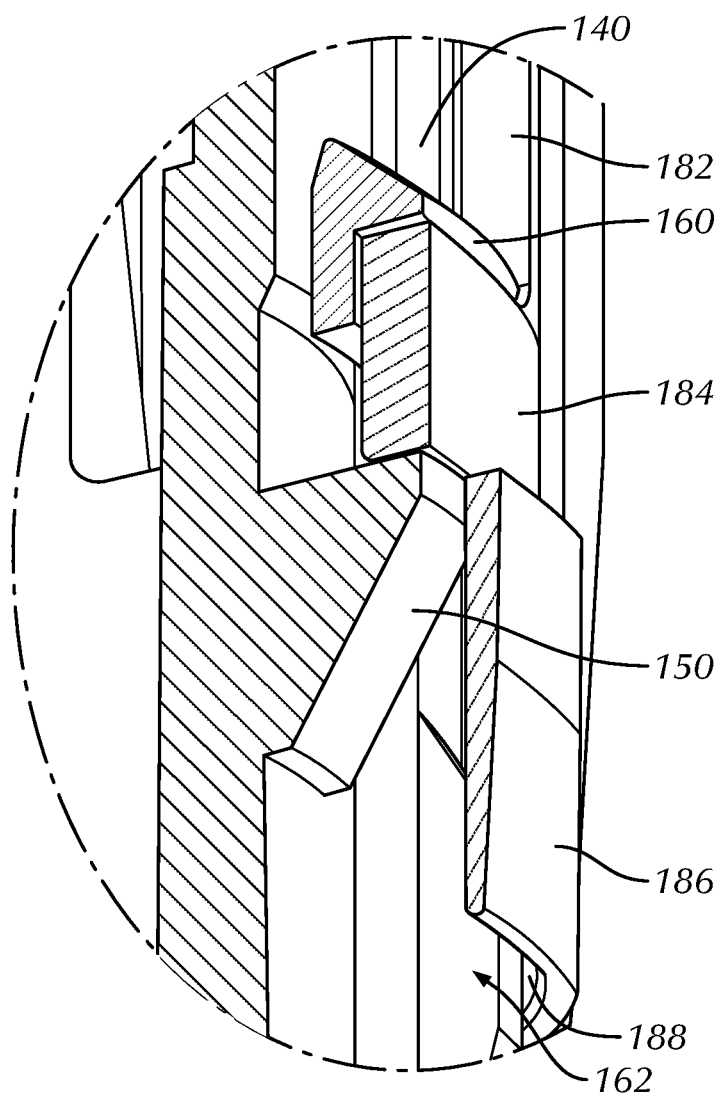
FIG. 16 is a greatly enlarged, partial cross-sectional left side perspective view of the lower housing, upper housing, and needle guard of FIGS. 13-15 in an initial position.
Figure 17:
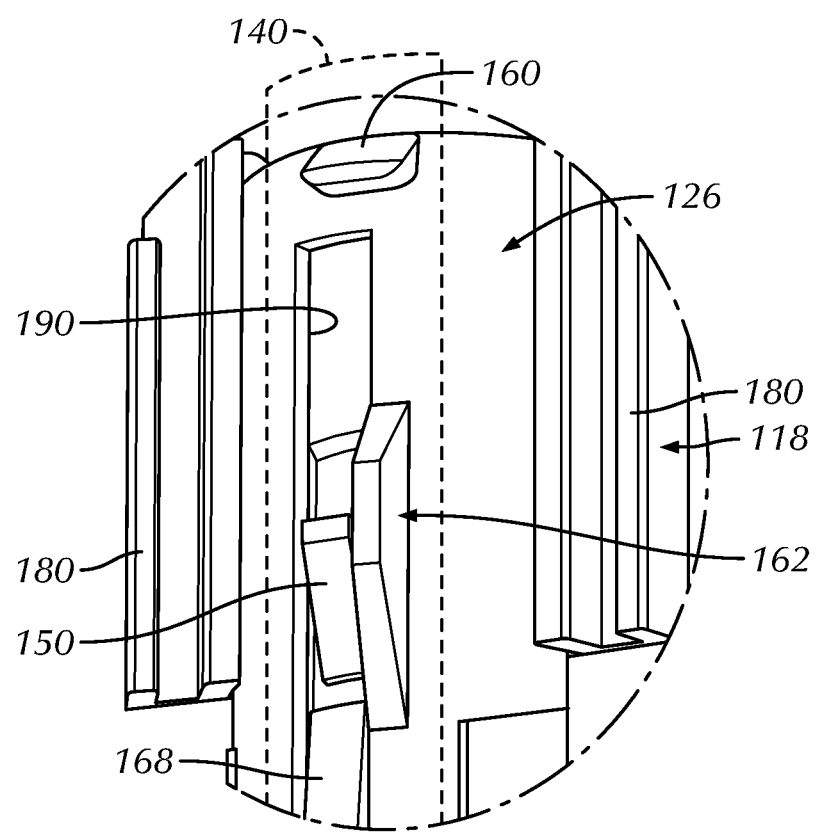
FIG. 17 is an enlarged, partial left side perspective view of the lower housing and needle guard of FIGS. 13 and 15 with the needle guard in the retracted position.

Referring to FIG. 16, in the initial position of the device, a distally facing surface of the free end 184 of the flap 182 of the upper housing 116 abuts a proximally facing surface of the catch 150 of the lower housing 118. Thus, distally directed pressure on the upper housing 116 will be unable to advance the upper housing 116 toward the distal end of the lower housing 118, and will consequently prevent advancement of the plunger through the prefilled syringe prior to the time of injection. In this initial position, the catch 150 of the lower housing 118 preferably resides within the pocket 188 at the distal end of the arm 134, i.e., radially inside of the bridge 186. The rim 160 of the needle guard 126 preferably resides within the track window 140 in this initial position. Depending on the location and sizing of components, a portion of the cam ramp 162 may also be located within the pocket 188 of the arm 134 in this initial position.

Similar to the earlier embodiment, when the needle guard 126 is placed at the injection site and distal pressure is applied, the needle guard 126 will retract into the lower housing 118, causing the cam ramp 162 to move proximally with respect to the catch 150 and the free end 184 of the flap 182. As the cam ramp 162 passes the proximally facing surface of the catch 150, the cam ramp 162 preferably interacts with the free end 184 of the flap 182, urging the free end 184 of the flap 182 radially outwardly. When the needle guard 126 reaches its retracted position, the plateau 166 of the cam ramp 162 is preferably in contact with the free end 184 of the flap 182. This interaction preferably displaces the free end 184 of the flap 182 radially outwardly by a distance sufficient to release from the catch 150 on the lower housing 118, allowing the free end 184 of the flap 182 to pass radially outside of the catch 150. In this way, further distally directed pressure on the upper housing 116 results in movement of the upper housing 116 toward the distal end of the lower housing 118, resulting in injection of the medicament from the prefilled syringe. As the free end 184 of the flap 182 distally clears the cam ramp 162, the free end 184 of the flap 182 returns to its original position, and the cam ramp 162 and the catch 150 both enter the track window 140 so as to avoid further radial interaction with the arm 134 during the injection. Although the upper housing 116 is not shown in FIG. 17, portions of the lower housing 118 and the needle guard 126 are shown with the needle guard 126 fully retracted, and the track window 140 is shown in phantom lines.

Figure 18:
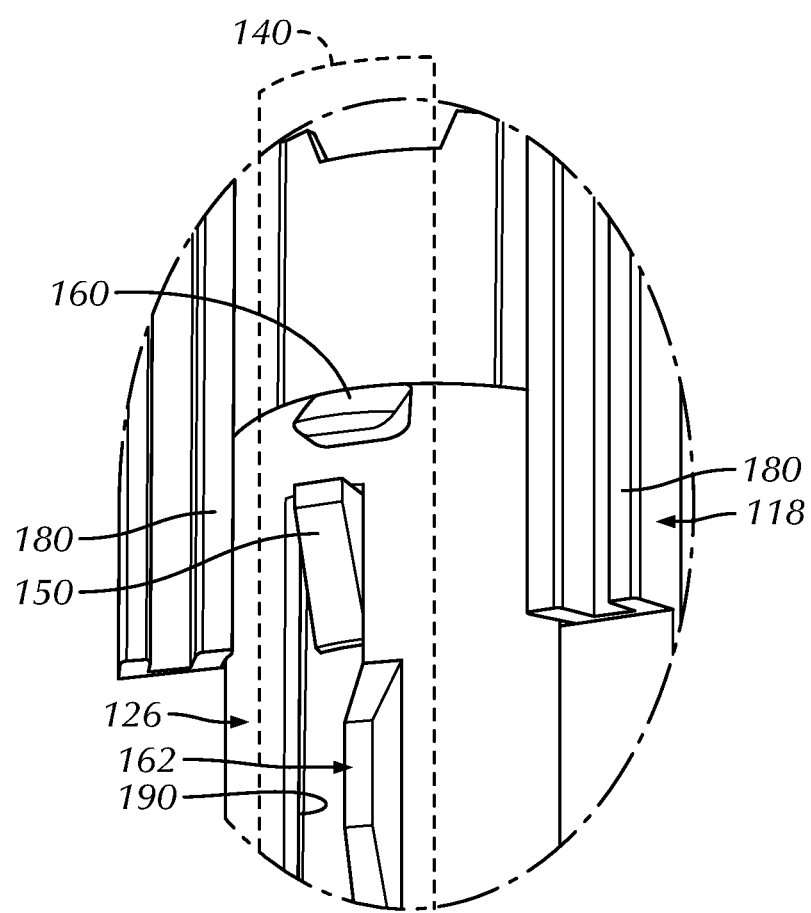
FIG. 18 is an enlarged, partial left side perspective view of the lower housing and needle guard of FIGS. 13 and 15 with the needle guard in the locked position.

FIG. 18 is a similar view of the device (i.e., with the upper housing 116 not shown, but the track window 140 shown in phantom lines), but following injection, where the needle guard 126 has fully extended with respect to the lower housing 118. In the embodiment shown in FIG. 18, further distal movement of the needle guard 126 with respect to the lower housing 118 is prevented by the proximally facing surface of the catch 150 coming into contact with a distally facing edge of the aperture 190 on the needle guard 126. Such contact is not possible in the initial position because the free end 184 of the flap 182 abutted the rim 160 of the needle guard 126. With the free end 184 of the flap 182 out of the way, the catch 150 can travel further proximally within the aperture 190, to allow full extension of the needle guard 126. In addition, subsequent retraction of the needle guard 126 is prevented by abutment of a proximally facing surface of the free end 172 (FIG. 15) of the locking finger 168 with a locking edge (not shown) of the lower housing 118, similar to the earlier embodiment.

While specific and distinct embodiments have been shown in the drawings, various individual elements or combinations of elements from the different embodiments may be combined with one another while in keeping with the spirit and scope of the invention. Thus, an individual feature described herein only with respect to one embodiment should not be construed as being incompatible with other embodiments described herein or otherwise encompassed by the invention.

It will be appreciated by those skilled in the art that various modifications and alterations could be made to the embodiments described above without departing from the broad inventive concepts thereof. Some of these have been discussed above and others will be apparent to those skilled in the art. It is understood, therefore, that this invention is not limited to the particular embodiments disclosed, but it is intended to cover modifications within the spirit and scope of the present disclosure, as set forth in the appended claims.

I claim:

1. An injection device configured to administer a medication, the injection device comprising:
   a lower housing configured to coaxially support a syringe that is configured to retain the medication, the syringe comprising a needle, wherein the needle protrudes from a distal end of the lower housing when the syringe is installed in the lower housing, the lower housing comprising a catch that extends at least partially radially outwardly, the catch comprising a proximally facing surface;
a needle guard in coaxial sliding engagement with the lower housing, the needle guard being longitudinally movable relative to the lower housing in a proximal direction from a first position, wherein a distal end of the needle guard extends distally beyond the distal end of the lower housing and the distal end of the needle guard is configured to conceal a distal tip of the needle when the syringe is installed in the lower housing, to a second position, wherein the distal end of the needle guard is configured to expose the distal tip of the needle when installed, the needle guard comprising:
a distal guard portion defining a distally facing needle opening;
a leg that extends proximally and longitudinally from the distal guard portion;
a rim that extends radially outwardly from the leg; and
a camming ramp that extends radially outwardly from the leg and that is positioned distally from the rim; and
an upper housing comprising an arm that extends longitudinally and that comprises an abutment body that comprises a distally facing abutment surface, the upper housing being in coaxial sliding engagement with the lower housing and longitudinally movable relative to the lower housing in a distal direction from a pre-use position to a dispensed position, wherein:
when the upper housing is in the pre-use position and the needle guard is in the first position, the distally facing abutment surface of the abutment body of the arm of the upper housing abuts the proximally facing surface of the at least one catch of the lower housing, which prevents the upper housing from moving distally relative to the lower housing toward the dispensed position, and the camming ramp of the leg of the needle guard is located distally of the catch of the lower housing, and
proximal movement of the needle guard from the first position to the second position causes proximal movement of the camming ramp with respect to the catch and the abutment body such that the camming ramp engages the arm and the abutment body of the arm deflects radially outwardly by a distance sufficient to allow the abutment body to pass radially outside of the catch of the lower housing and, in turn, permits distal movement of the upper housing relative to the lower housing into the dispensed position of the upper housing.

2. The injection device of claim 1, wherein a distally facing surface of the rim of the leg of the needle guard abuts a proximally facing surface of the abutment body of the arm of the upper housing in the pre-use position of the upper housing and the first position of the needle guard, which prevents movement of the needle guard in the distal direction relative to the lower housing.

3. The injection device of claim 1, wherein the leg is a first leg and the needle guard comprises a second leg circumferentially spaced apart from the first leg, and the first leg and the second leg extend from opposing sides of a central longitudinal axis of the needle guard.

4. The injection device of claim 1, wherein the lower housing includes a bore that is oriented longitudinally and configured to receive and support the syringe.

5. The injection device of claim 1, further comprising a spring wherein:

the spring distally biases the needle guard relative to the upper housing and the lower housing, and
in the dispensed position of the upper housing and in absence of a force directed in the proximal direction applied to the needle guard that is greater than a biasing force of the spring, the needle guard is distally biased from the second position to a third position, whereby the rim of the leg of the needle guard abuts the catch of the lower housing and the distal end of the needle guard is configured to re-conceal the distal tip of the needle when installed.

6. The injection device of claim 5, wherein:
the lower housing includes a bore that extends longitudinally and that is configured to receive and support the syringe, the bore comprising a distal edge that is radially outwardly inclined,
the leg of the needle guard comprises a deflectable finger that is longitudinally oriented and that has a free proximal end that is radially inwardly biased, and
the free proximal end of the deflectable finger abuts with the distal edge of the bore of the lower housing in the third position of the needle guard, thereby preventing subsequent proximal movement of the needle guard relative to the lower housing.

7. The injection device of claim 5, wherein the distal guard portion of the needle guard comprises a visual indicator that is obscured from view by the lower housing in the first position of the needle guard and in the second position of the needle guard, and exposed from the lower housing in the third position of the needle guard.

8. The injection device of claim 7, wherein:
in the third position, the distal end of the needle guard extends distally beyond the distal end of the lower housing by a greater distance than in the first position, and
the visual indicator comprises an annular ring proximate a proximal end of the distal guard portion, the annular ring comprising at least one of a larger radial thickness than a remainder of the distal guard portion or a color different than the remainder of the distal guard portion.

9. The injection device of claim 1, wherein the camming ramp comprises a ridge that extends longitudinally, the ridge comprising a plateau with sloped portions that extend radially inwardly in both the proximal direction and the distal direction.

10. The injection device of claim 9, wherein the plateau of the camming ramp engages the abutment body of the arm of the upper housing in the second position of the needle guard.

11. The injection device of claim 9, wherein the ridge that extends longitudinally comprises a pair of ridges that extend longitudinally.

12. The injection device of claim 1, wherein the arm of the upper housing is a first arm and the upper housing comprises a second arm that extends longitudinally and that is circumferentially spaced apart from the first arm, the first arm and the second arm extend from opposing sides of a central longitudinal axis of the upper housing.

13. The injection device of claim 11, wherein the lower housing comprises track walls that are circumferentially spaced apart and that extend longitudinally, the track walls bracketing tracks that are spaced apart and extend longitudinally, and that are configured to each receive a corresponding one of the first arm and the second arm for rotationally fixed, longitudinal movement within the tracks, and wherein each track of the tracks includes one or more of the catch.

14. The injection device of claim 1, wherein the rim is a barbed rim projecting distally from a proximal end of the leg.

15. The injection device of claim 1, wherein the abutment body comprises a ledge that extends radially inwardly proximate a distal end of the arm.

16. The injection device of claim 15, wherein the ledge includes a locking tab extending further radially inwardly from other portions of the ledge, wherein the distally facing abutment surface comprises a distally facing surface of the locking tab.

17. The injection device of claim 1, wherein:
the arm of the upper housing includes a flap that extends longitudinally,
the distally facing abutment surface comprises a distally facing surface of a free distal end of the flap,
the arm of the upper housing includes a bridge proximate a distal end of the arm, the bridge extending further radially outwardly than the free distal end of the flap, forming an underlying pocket, and
the free distal end of the flap abuts the catch of the lower housing in the pre-use position of the upper housing and the first position of the needle guard.

18. The injection device of claim 1, wherein the lower housing includes rails that extend longitudinally and that are configured to receive opposing longitudinal edges of the arm of the upper housing for rotationally fixed, longitudinal movement within the rails, and wherein the catch is positioned between the rails.

\* \* \* \* \*